(12) United States Patent
Zayicek et al.

(10) Patent No.: US 6,736,011 B2
(45) Date of Patent: May 18, 2004

(54) INSPECTION OF SHRUNK-ON STEAM TURBINE DISKS USING ADVANCED ULTRASONIC TECHNIQUES

(75) Inventors: Paul A. Zayicek, Gastonia, NC (US); Greg P. Selby, Charlotte, NC (US); Mark A. Dennis, Charlotte, NC (US)

(73) Assignee: Electric Power Research Institute, Inc., Palo Alto, CA (US)

( * ) Notice: Subject to any disclaimer, the term of this patent is extended or adjusted under 35 U.S.C. 154(b) by 78 days.

(21) Appl. No.: 10/007,123

(22) Filed: Dec. 4, 2001

(65) Prior Publication Data

US 2002/0088282 A1 Jul. 11, 2002

Related U.S. Application Data

(60) Provisional application No. 60/254,372, filed on Dec. 7, 2000.

(51) Int. Cl.[7] ................................................ G01N 29/00
(52) U.S. Cl. ............................................. 73/628; 73/633
(58) Field of Search .......................... 73/627, 628, 629, 73/632, 633, 640, 644, 642, 641, 624, 618, 620, 621, 625, 626

(56) References Cited

U.S. PATENT DOCUMENTS

| | | | |
|---|---|---|---|
| 3,995,968 A | * 12/1976 | Campbell, Jr. et al. | ........ 73/629 |
| 4,353,258 A | * 10/1982 | Hunter | ......................... 73/644 |
| 4,502,331 A | * 3/1985 | Singh et al. | ................... 73/627 |
| 4,977,780 A | * 12/1990 | Machida et al. | .............. 73/644 |
| 6,082,198 A | 7/2000 | Sabourin et al. | |

* cited by examiner

*Primary Examiner*—Helen Kwok
(74) *Attorney, Agent, or Firm*—Dorsey & Whitney LLP

(57) ABSTRACT

A method of ultrasonically testing the disk bore and keyway area of a shrunk-on steam turbine rotor disk or hub is provided. The method employs a one or more scanning ultrasonic phased linear array probes mounted on the disk to inspect the disk bore and keyway area on the opposite side of the disk.

10 Claims, 3 Drawing Sheets

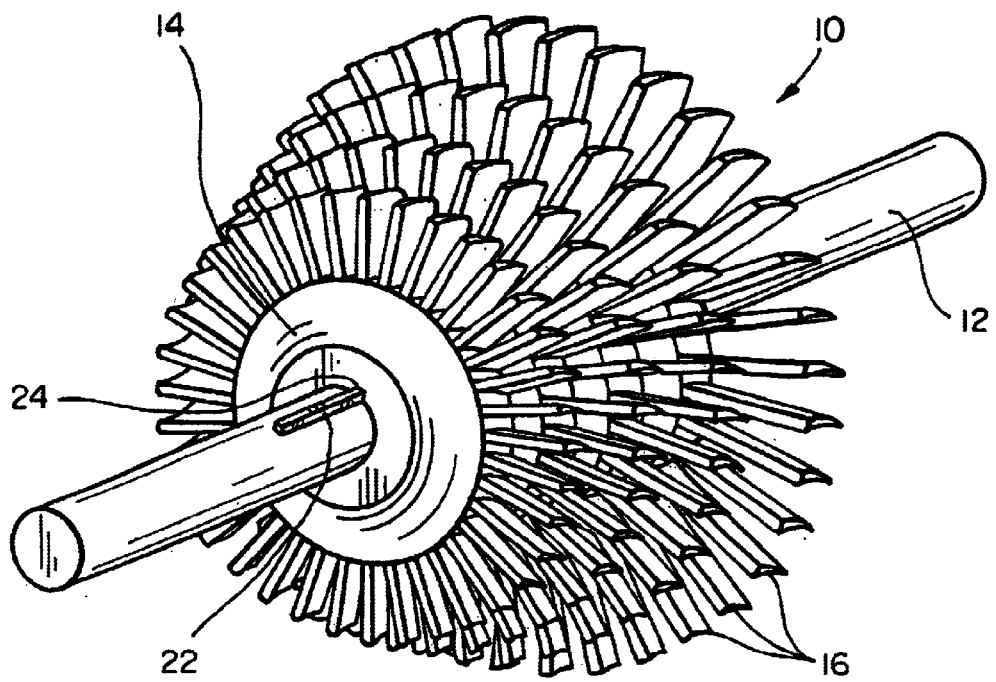
FIG_1
(PRIOR ART)
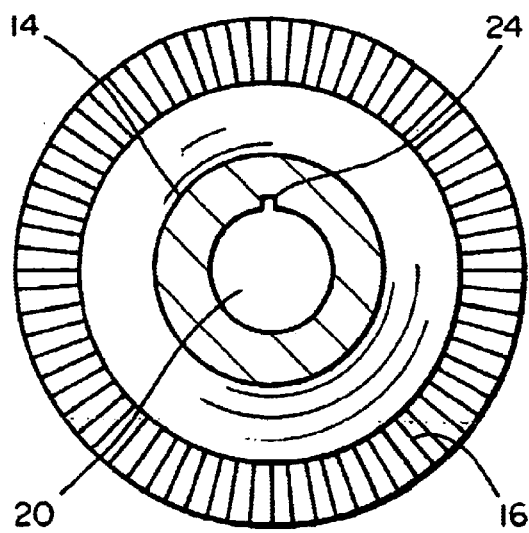
FIG_2
(PRIOR ART)

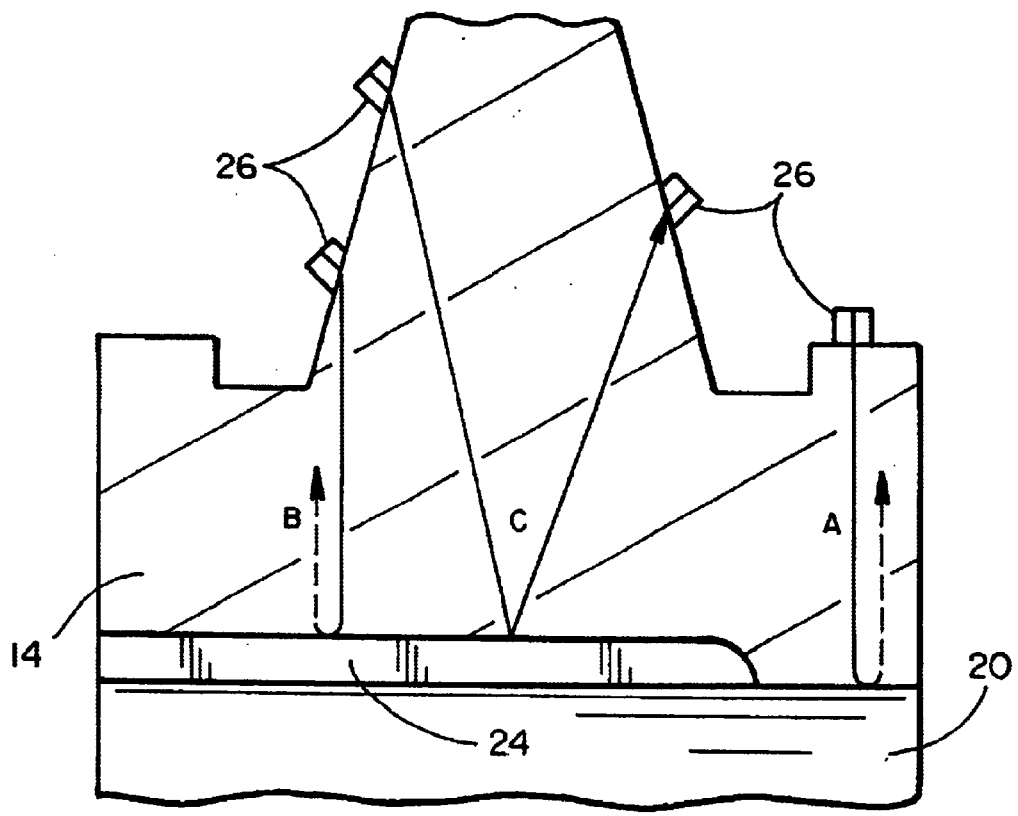
FIG_3A
*(PRIOR ART)*
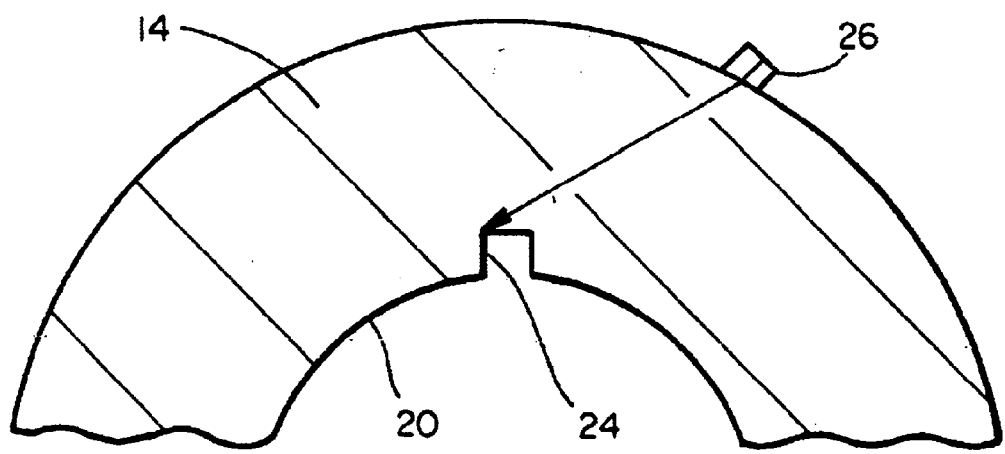
FIG_3B
*(PRIOR ART)*

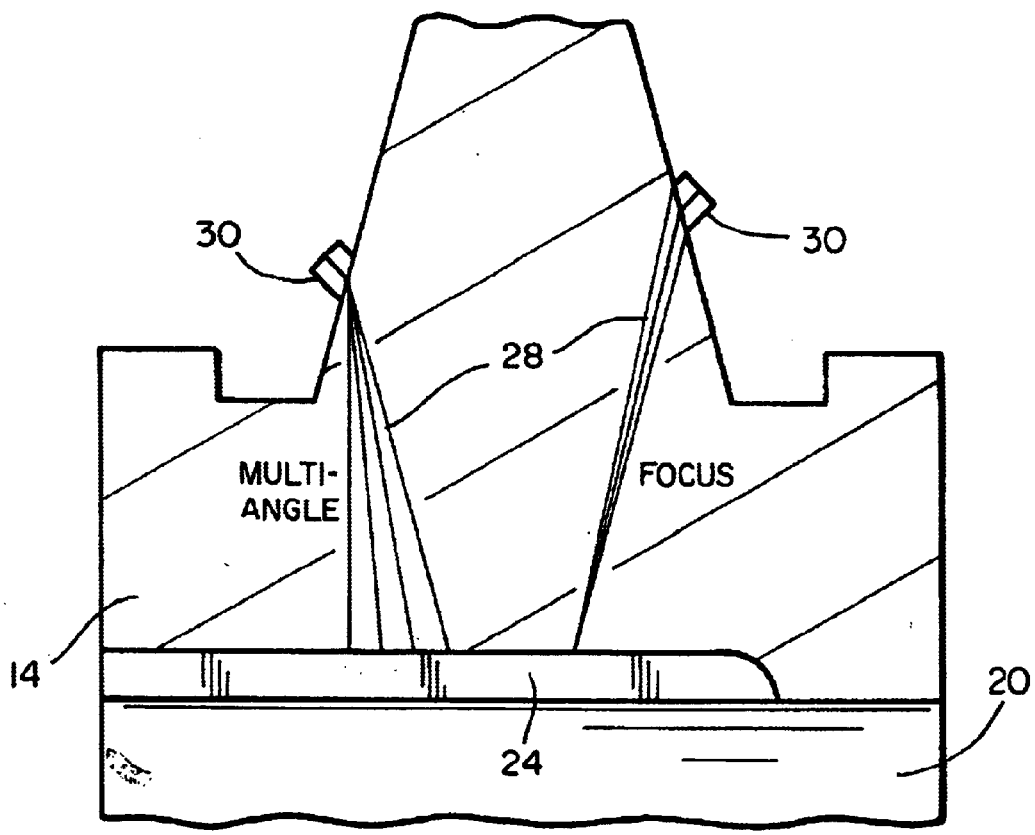
FIG_4A
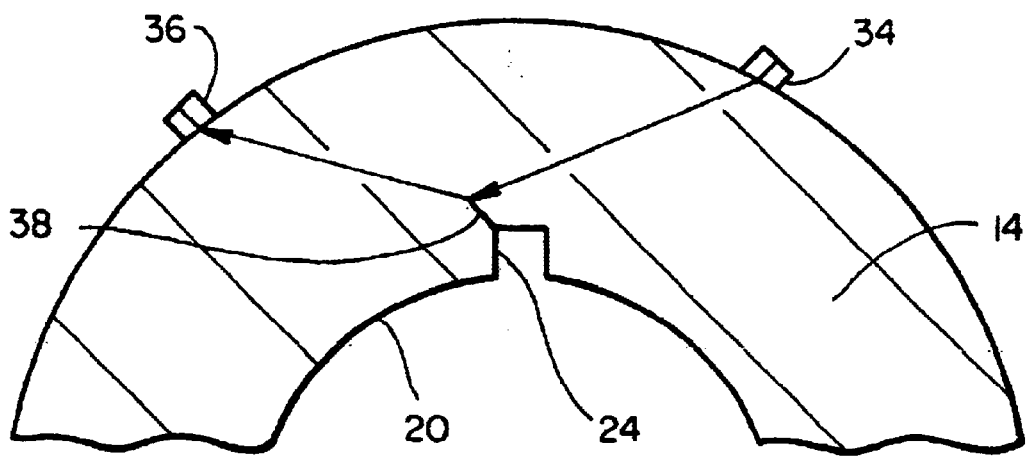
FIG_4B

INSPECTION OF SHRUNK-ON STEAM TURBINE DISKS USING ADVANCED ULTRASONIC TECHNIQUES

RELATED APPLICATIONS

This application claims priority to U.S. Provisional Application Serial No. 60/254,372 filed Dec. 7, 2000.

BRIEF DESCRIPTION OF THE INVENTION

This invention relates generally to ultrasonic inspection of shrunk-on steam turbine disks or hubs and more particularly to the ultrasonic inspection of the disk bore and keyway area to detect stress corrosion cracking.

BACKGROUND OF THE INVENTION

Turbines are used to generate rotary mechanical power from the energy in a working fluid. The working fluid energy, originally in the form of pressure energy, is converted to velocity energy by passing through a system of blades in the turbine. Changes in the magnitude and direction of the velocity energy are made to cause tangential forces on the blades to produce mechanical rotation of the turbine rotor. The rotating turbine rotor may be coupled to a generator rotor and stator to produce electricity.

Steam turbines are used to convert thermal energy into usable work and are typically used to drive alternating current electric generators. A large number of "built-up" low pressure, steam turbine rotors are operating in the U.S. electric utility industry. FIG. 1 and FIG. 2 illustrate an example of a simplified rotor assembly. A built-up rotor 10 generally consists of a large central rotor shaft 12 with individual disks or blade hubs 14 fitted to the shaft. Individual disks carry one or more stages of blades 16, or buckets, that capture the incoming steam and transform it to torsional energy. The disks have a central bore hole 20 that matches a specific machined step on the central shaft as illustrated in FIG. 2. The disks are typically shrunk onto the shaft and subsequently restrained from torsional movement, relative to the shaft, by use of a key 22. A machined slot, or keyway 24, cut into the disk and shaft accommodates the key. Utility operating experience with built-up rotors using shrunk-on disks has demonstrated that the area around the central bore hole 20 of the disk or hub 14, and especially the area around the keyway 24 on the rotor hub 14, are subject to stress corrosion cracking (SCC) that can ultimately lead to catastrophic failure.

A variety of ultrasonic inspection techniques are used to examine various components that make up a steam turbine rotor. One method using phased array ultrasonic sensors to inspect turbine blade attachments is described in U.S. Pat. No. 6,082,198 the text of which is hereby incorporated by reference. Ultrasonic techniques involve applying high frequency sound waves to a structure of interest. When the sound waves interact with an object that has a significant difference in acoustic impedance (the product of density and acoustic velocity) from that of the propagation medium, a portion of the sound is either reflected or diffracted back to the source from which the sound originated. Detection and quantification of the returned sound pattern is used to determine the presence and characteristics of the reflecting medium.

Ultrasonic inspections of the disk bore 20 and keyway area 24 have historically been performed to detect SCC as illustrated in FIGS. 3A and 3B. The keyway area is the highest stress point on the disk bore, so substantial effort is invested in detecting and sizing cracks in this area. Current state of the art techniques for inspection of the disk bore area use a series of individual, conventional, single angle, ultrasonic probes 26. These probes 26 are placed on the disk face and angled to transmit toward the keyway area 24. Reflections and diffractions from the area and the disk edges are recorded automatically or manually and then analyzed in relation to the known geometry of the keyway area. These prior art methods are most effective if used in conjunction with detailed existing data on the geometry of the keyway area. Additionally, because of the need for numerous probes operating at fixed angles, the process is relatively slow and can only be performed while the turbine is out of service.

SUMMARY OF THE INVENTION

Accordingly, it is a general object of the present invention to provide a method for using advanced ultrasonic techniques to inspect the disk bore and keyway area of a shrunk-on steam turbine disk.

More specifically, it is an object of the current invention to provide a method employing linear phased array probe technology to ultrasonically inspect the disk bore and keyway area of a shrunk-on steam turbine disk.

Alternatively, it is an object of the present invention to provide a method for ultrasonically inspecting the disk bore and keyway area of a shrunk-on steam turbine disk that employs time of flight diffraction (TOFD) techniques.

BRIEF DESCRIPTION OF THE DRAWINGS

The invention will be better understood from the following description which reads in the conjunction with the accompanying drawings as follows.

FIG. 1 is a schematic perspective view of a rotor assembly.

FIG. 2 is a cross sectional view perpendicular to the rotor of a shrunk-on steam turbine disk with a keyway.

FIG. 3A is a cross sectional view along the rotor's axis of a shrunk-on steam turbine disk illustrating a prior art method of ultrasonically inspecting the disk bore and keyway area using a series of individual, single angle ultrasonic probes.

FIG. 3B is a cross sectional view perpendicular to the rotor of a shrunk-on steam turbine disk illustrating a prior art method of ultrasonically inspecting the disk bore keyway area using an individual, single angle ultrasonic probe.

FIG. 4A is a cross sectional view along the rotor's axis of a shrunk-on steam turbine disk illustrating the method of ultrasonically inspecting the disk bore and keyway area using linear phased array probes.

FIG. 4B is a cross sectional view perpendicular to the rotor of a shrunk-on steam turbine disk illustrating the method of ultrasonically inspecting the disk bore and keyway area using time of flight diffraction probes.

DESCRIPTION OF THE INVENTION

The present invention uses a linear ultrasonic array probe 30 for detecting or inspecting for SCC. The linear array probe 30 is a series of individual, small ultrasonic transducers arranged in a row. Each transducer element has its own electrical connections and is acoustically isolated from the other elements. Each element has its own pulser/receiver circuit and produces its own radio frequency, time/amplitude response, called an "A-scan." The angle of the beam is controlled by modulating the timing of the pulses and reception by each transducer element. The individual A-scans from each transducer in the array are summed and the resulting A-scan is saved. The angle, mode and focus of the ultrasonic beam are varied by controlling the timing pulse and reception for each element before the individual element responses are summed. With the turbine fully assembled, one or more array probes are placed on one or both faces of the turbine rotor hub or disk 14. The probe or probes successively generate longitudinal mode or shear mode sound beams, or both, in one degree increments as illustrated schematically in FIG. 4A. In one embodiment the probe 30 scans over a range of beam angles, for example from 30 to 80 degrees (labeled "multi-angle" in FIG. 4A). Scanning a range of angles allows increased coverage of the disk bore 20 and keyway interface area 24. The total length of the disk bore 20 and keyway are 24 can be examined with a single probe. In an alternative embodiment, beam focusing as shown in FIG. 4A may be used to improve quantification of the length and depth of a specific defect.

Use of a linear array probe provides better signal to noise ratio and a more concise beam profile resulting in improved detection, sizing, and characterization of service induced flaws as compared to current inspection practices.

Another preferred embodiment of the current invention is a method that employs time of flight diffraction (TOFD). TOFD is a variation of the "pitch and catch" technique presented above in which a first array probe 34 that can be a scanning transmitting transducer and a second array probe 36 that can be a scanning receiving transducer are used as shown in FIG. 4B. Transmitted ultrasonic energy from the transmitting transducer 34 is diffracted from the tip of a crack and also transmitted along the scanning surface and reflected from the backwall. The receiving transducer 36 detects and quantifies the diffracted and transmitted ultrasonic energy. Data collected by this second probe 36 is assembled to recreate an image of the keyway area 24. The resulting image shows the structure of the keyway area 24 and can be analyzed to identify the presence of defects or cracks 38. TOFD can also be used to inspect the remainder of the disk bore interface. One advantage of TOFD over the conventional pulse echo method in which the same array probe both transmits and receives the ultrasonic energy is that TOFD is substantially less sensitive to flaw orientation. TOFD may also offer an advantage in more accurately determining the depth and length of cracks.

The attributes of advanced ultrasonic inspection techniques should help in more accurately determining the remaining service life of individual disks and allow for more efficient inspection and repair planning over the useful life of the disks.

In general, cracks that occur for the rotor geometry shown in FIGS. 1 and 2 initiate on the disk bore in the radial direction on the disk bore 20 or on a parallel plane in the keyway area 24. As such, in an advantageous embodiment of the present invention, inspection probes 30 are positioned to send an incident beam perpendicular to the expected flaw orientation, a skewed position to allow a corner trap beam, and a radial position for crack tip detection. Experiments conducted by the inventors have indicated that the use of two separate phased array probes 30 positioned on opposite faces of the rotor disk 14 and operating in the aforementioned pitch and catch mode provides the most complete inspection coverage of the disk bore 20 and keyway area 24.

The foregoing descriptions of specific embodiments of the present invention are presented for purposes of illustration and description. They are not intended to be exhaustive or to limit the invention to the precise forms disclosed. Obviously many modifications and variations are possible in view of the above teachings. The embodiments were chosen and described to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

What is claimed is:

1. The method of ultrasonically inspecting an area around a disk bore and a keyway on a shrunk-on steam turbine disk that is attached to a rotor comprising the steps of:

placing one or more phased array ultrasonic probes on at least one face of said disk across from said keyway area without disassembling said disk from said rotor, transmitting ultrasonic energy in the form of one or more beams from said one or more ultrasonic probes to scan along said disk bore and keyway area, detecting and quantifying reflected and diffracted energy from structures in said disk bore and keyway area to simultaneously reconstruct an image of said disk bore and keyway area, and using said image to detect and locate defects within said disk bore and keyway area.

2. The method of claim 1 wherein:

said one or more probes successively generate longitudinal-mode or shear-mode sound beams or both.

3. The method of claim 1 wherein:

said one or more probes include a plurality of transducer elements, each of said transducer elements including a pulser/receiver circuit; and the angle of said one or more beams is controlled by modulating the timing of pulse emissions and reception by each of said transducer elements.

4. The method of claim 1 wherein:

said one or more probes are positioned axially from said keyway area so that transmitted ultrasonic energy is diffracted from a tip of a crack and transmitted along, a scanning surface in said disk bore and keyway area.

5. The method of claim 1 wherein:

said one or more probes are arranged so that transmitted ultrasonic energy is perpendicularly incident on a crack.

6. The method of claim 1 wherein said one or more probes are arranged in a skewed position from said keyway area so that transmitted ultrasonic energy is forms a corner trap.

7. The method of ultrasonically inspecting an area around a disk bore and a keyway on a shrunk-on steam turbine disk that is attached to a rotor comprising the steps of:

placing one or more phased array ultrasonic probes on one or more faces of said disk across from said keyway area without disassembling said disk from said rotor;

transmitting ultrasonic energy from said one or more ultrasonic probes to scan along said disk bore and keyway area, said one or more probes successively generating one or more longitudinal-mode or shear-mode sound beams or both, said one or more probes further including a plurality of transducer elements, each of said transducer elements including a pulser/receiver circuit and in which an angle of said one or more beams is controlled by modulating the timing of pulse emissions and reception by each transducer element;

detecting and quantifying reflected and diffracted energy from structures in said keyway area to simultaneously reconstruct an image of said disk bore and keyway area; and using said image to detect and locate defects within said disk bore and keyway area.

8. The method of ultrasonically inspecting an area around a disk bore and a keyway on a shrunk-on steam turbine disk that is attached to a rotor comprising the steps of:

placing a first phased array ultrasonic probe on one face of said disk, said first probe operating as a scanning transmitting transducer, and a second phased array ultrasonic probe on the same face of said disk opposite said first probe across from said keyway area, said second probe operating as a receiving transducer, without disassembling said disk from said rotor;

transmitting ultrasonic energy in the form of one or more beams from said first probe to scan along said disk bore and keyway area;

detecting and quantifying reflected and diffracted energy from structures in said disk bore and keyway area with said second probe to simultaneously reconstruct an image of said disk bore and keyway area; and using said image to detect and locate defects within said disk bore and keyway area.

9. The method of claim 8 wherein:

said first probe successively generates longitudinal-mode or shear-mode sound beams or both.

10. The method of claim 8 wherein:

said first and second probes each include a plurality of transducer elements, each of said transducer elements including a pulser/receiver circuit; and an angle of said one or more beams is controlled by controlling the timing of pulse emissions and reception by each transducer element.

* * * * *